(12) United States Patent
Hufford

(10) Patent No.: US 11,690,677 B2
(45) Date of Patent: Jul. 4, 2023

(54) USE OF EYE TRACKING FOR TOOL IDENTIFICATION AND ASSIGNMENT IN A ROBOTIC SURGICAL SYSTEM

(71) Applicant: Asensus Surgical US, Inc., Durham, NC (US)

(72) Inventor: Kevin Andrew Hufford, Cary, NC (US)

(73) Assignee: Asensus Surgical US, Inc., Durham, NC (US)

( * ) Notice: Subject to any disclaimer, the term of this patent is extended or adjusted under 35 U.S.C. 154(b) by 237 days.

(21) Appl. No.: 16/237,418

(22) Filed: Dec. 31, 2018

(65) Prior Publication Data
US 2019/0201107 A1    Jul. 4, 2019

Related U.S. Application Data

(60) Provisional application No. 62/612,554, filed on Dec. 31, 2017.

(51) Int. Cl.
| | |
|---|---|
| *G05B 15/00* | (2006.01) |
| *G05B 19/00* | (2006.01) |
| *A61B 34/20* | (2016.01) |
| *A61B 34/30* | (2016.01) |
| *A61B 90/00* | (2016.01) |
| *G06F 3/01* | (2006.01) |
| *A61B 34/37* | (2016.01) |
| *B25J 9/16* | (2006.01) |
| *B25J 9/00* | (2006.01) |
| *B25J 9/02* | (2006.01) |

(Continued)

(52) U.S. Cl.
CPC .............. *A61B 34/20* (2016.02); *A61B 34/30* (2016.02); *A61B 34/37* (2016.02); *A61B 90/361* (2016.02); *A61B 90/37* (2016.02); *B25J 9/0021* (2013.01); *B25J 9/023* (2013.01); *B25J 9/16* (2013.01); *B25J 9/1682* (2013.01); *B25J 9/1697* (2013.01); *G06F 3/013* (2013.01); *A61B 34/76* (2016.02); *A61B 2017/00216* (2013.01); *A61B 2034/2055* (2016.02); *A61B 2034/305* (2016.02)

(58) Field of Classification Search
CPC .... G06F 3/013; G06F 3/04842; B25J 9/0021; B25J 9/023; B25J 9/16; B25J 9/1682; B25J 9/1697; A61B 2017/00216; A61B 2034/2055; A61B 34/20; A61B 34/30; A61B 34/76; A61B 90/361; A61B 90/37; A61B 2034/305; A61B 34/37
See application file for complete search history.

(56) References Cited

U.S. PATENT DOCUMENTS

| | | | | |
|---|---|---|---|---|
| 10,265,057 B2 * | 4/2019 | Herzlinger | ......... | A61B 1/00039 |
| 10,278,782 B2 * | 5/2019 | Jarc | .................... | G02B 27/0093 |
| 10,432,922 B2 * | 10/2019 | Jarc | ....................... | G02B 30/35 |

(Continued)

*Primary Examiner* — Harry Y Oh

(57) ABSTRACT

A robotic surgical system includes an eye gaze sensing system in conjunction with a visual display of a camera image from a surgical work site. Detected gaze of a surgeon towards the display is used as input to the system. This input may be used by the system to assign an instrument to a control input device (when the user is prompted to look at the instrument), or it may be used as input to a computer vision algorithm to aid in object differentiation and seeding information, facilitating identification/differentiation of instruments, anatomical features or regions.

8 Claims, 9 Drawing Sheets

(51) Int. Cl.
 *A61B 34/00* (2016.01)
 *A61B 17/00* (2006.01)

(56) References Cited

U.S. PATENT DOCUMENTS

| | | | |
|---|---|---|---|
| 10,682,038 B1* | 6/2020 | Zhang | G06F 3/013 |
| 2012/0069166 A1* | 3/2012 | Kunz | G06F 3/013 |
| | | | 348/E7.085 |
| 2013/0030571 A1* | 1/2013 | Ruiz Morales | A61B 17/00 |
| | | | 700/259 |
| 2014/0024889 A1* | 1/2014 | Xiaoli | A61B 34/30 |
| | | | 600/102 |
| 2016/0112414 A1* | 4/2016 | Tsou | H04L 63/083 |
| | | | 726/7 |
| 2016/0183930 A1* | 6/2016 | Herzlinger | G06F 3/0338 |
| | | | 600/118 |

\* cited by examiner

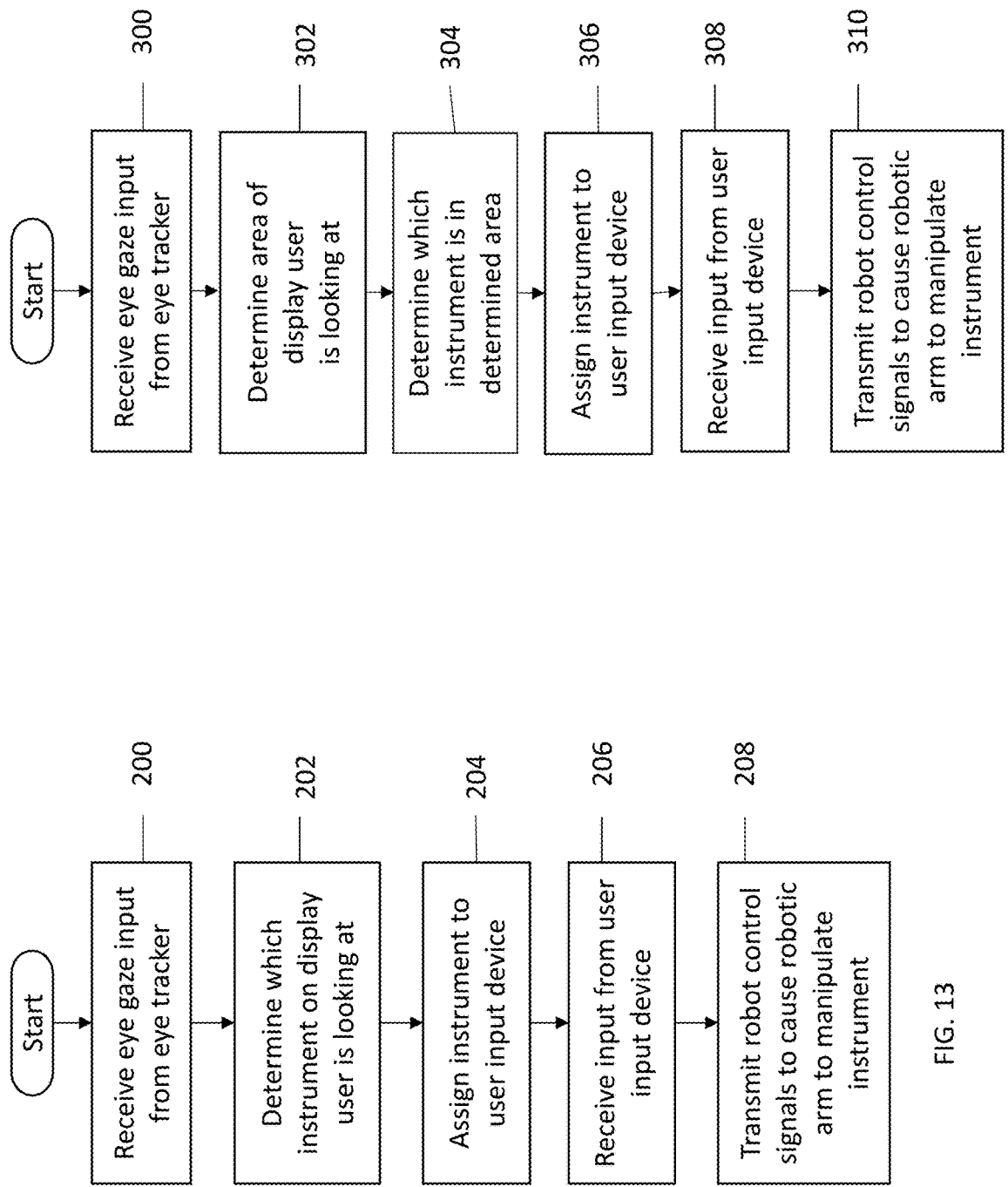

USE OF EYE TRACKING FOR TOOL IDENTIFICATION AND ASSIGNMENT IN A ROBOTIC SURGICAL SYSTEM

TECHNICAL FIELD OF THE INVENTION

The present invention relates generally to the use of eye tracking in surgical robotic systems.

BACKGROUND

US Published Application No. 2013/0030571 (the '571 application), which is owned by the owner of the present application and which is incorporated herein by reference, describes a robotic surgical system that includes an eye tracking system. The eye tracking system detects the direction of the surgeon's gaze and enters commands to the surgical system based on the detected direction of the gaze.

FIG. 1 is a schematic view of the prior art robotic surgery system 10 of the '571. The system 10 comprises at least one robotic arm which acts under the control of a control console 12 managed by the surgeon who may be seated at the console. The system shown in FIG. 1 includes multiple robotic arms 11a, 11b, 11c. Three such arms are shown but a larger or smaller number may be used. Each robotic arm can support and operate a surgical instrument 14, 15, 16 for use on a patient 13. One of the instruments 14 is preferably a camera which records the operating field inside the patient, while the other instruments may be known surgical tools 15, 16.

The arms 11a, 11b, 11c are operated by an electronic control unit 30 which causes the arms to perform the movements entered via the console 12. The unit 30 will receive the high-level movement commands (for example, desired position and inclination of the tool supported by the robot) and will execute them, converting them into the corresponding sequences of signals to be sent to the individual motors of the robot arm articulations. Other details of the system 10 are found in the '571 application which is fully incorporated herein by reference.

The console includes input devices 17, 18 which can be gripped by the surgeon and moved so as to deliver instructions to the system as to the desired movement and operation of the instruments supported by the arms 11a, 11b, 11c.

The surgeon's movements are suitably reproduced by the surgical instruments by means of movement of the robotic arms. The input devices may be equipped to provide the surgeon with tactile feedback so that the surgeon can feel on the input devices 17, 18 the forces exerted by the instruments on the patient's tissues.

Each input device will typically operate a robot arm. The '571 application describes that where there are two input handles and more than two arms carrying instruments, the system includes a control on the console that allows the surgeon to assign each arm to a desired instrument. This allows a surgeon to control of two of the surgical instruments disposed at the working site at any given time. To control a third instrument disposed at the working site, one of the two handles 17, 18 is operatively disengaged from one of the initial two instruments and then operatively paired with the third instrument.

The console may also include a keyboard 19 and/or touch screen and/or other command input devices. These other command devices might include a pedal device 20, and a button(s) on or in proximity to one or both handles of the input devices 17, 18.

The console 12 has an eye movement tracking system 21 or so-called "eye tracker" for detecting the direction of the surgeon's gaze towards the console and for controlling the surgical system depending on the gaze directions detected. In this way, the surgeon may control functions of the system by means of movement of his/her eyes.

The eye tracking system estimates the direction of the surgeon's gaze towards the display 22 and performs selection of the commands associated with a zone when it detects a gaze direction which falls within this zone. In one particular example described in the '571, the commands associated with selection areas 29 on the display 22 comprise the commands for assigning particular ones of the arms 11a, 11b, 11c to the surgeon input devices 17, 18. That allows the surgeon to alternate control of the robot arms on the two input devices without letting go of the input devices, but instead by simply looking at the corresponding selection areas on the screen. For example, while controlling each of the arms 11a, 11c with one of the input devices 17, 18, the user might re-assign input device 17 over to arm 11b in order to use or reposition the instrument 9b within the body. Once the task involving movement of instrument 9b is completed, the surgeon can rapidly re-assign input device 17 back to robot arm 11a. These steps can be performed by using the eye tracking features to "drag and drop" icons on the console display towards icons representing the various arms.

In another example described in the '571, the eye tracking system is used to move the camera based on where the surgeon is looking on the display 22. When this function is enabled (e.g. by entering an input command, such as through pressing of a button on the console, depressing a foot pedal, etc.), the movement of the eyes over the image of the operating field on the screen causes the movement of the robot arm supporting the camera. This can be used to place the zone the surgeon is focused on at the center of the display screen.

The '571 also describes use of the eye tracker to detect the distance between the screen and surgeon's eyes as a way to allow the surgeon to "zoom" the camera display in or out. The system enlarges the picture of the operating field shown on the screen depending on a variation in the distance detected. With this feature, the surgeon can intuitively perform enlargement of the picture by simply moving his/her face towards the screen and, vice versa, increase the viewing area of the operating field, thus reducing enlargement, by moving his/her face away from the screen.

BRIEF DESCRIPTION OF THE DRAWINGS

FIG. 13 is a flow diagram illustrating a first method of using eye tracking input to aid in assignment of a user input devices to and instrument or its corresponding robotic arm.

FIG. 14 is a flow diagram illustrating a second method of using eye tracking input to aid in assignment of a user input devices to and instrument or its corresponding robotic arm.

DETAILED DESCRIPTION

This application describes a system having features allowing differentiation of objects or regions on a displayed image, such as a surgical site, using eye gaze sensing as an input. In particular embodiments, it allows the use of eye tracking within a displayed image to aid in assignment of instruments to robotic manipulators, and/or to aid the system in using computer vision to recognize instruments shown on the endoscopic display.

System

Figure 1:
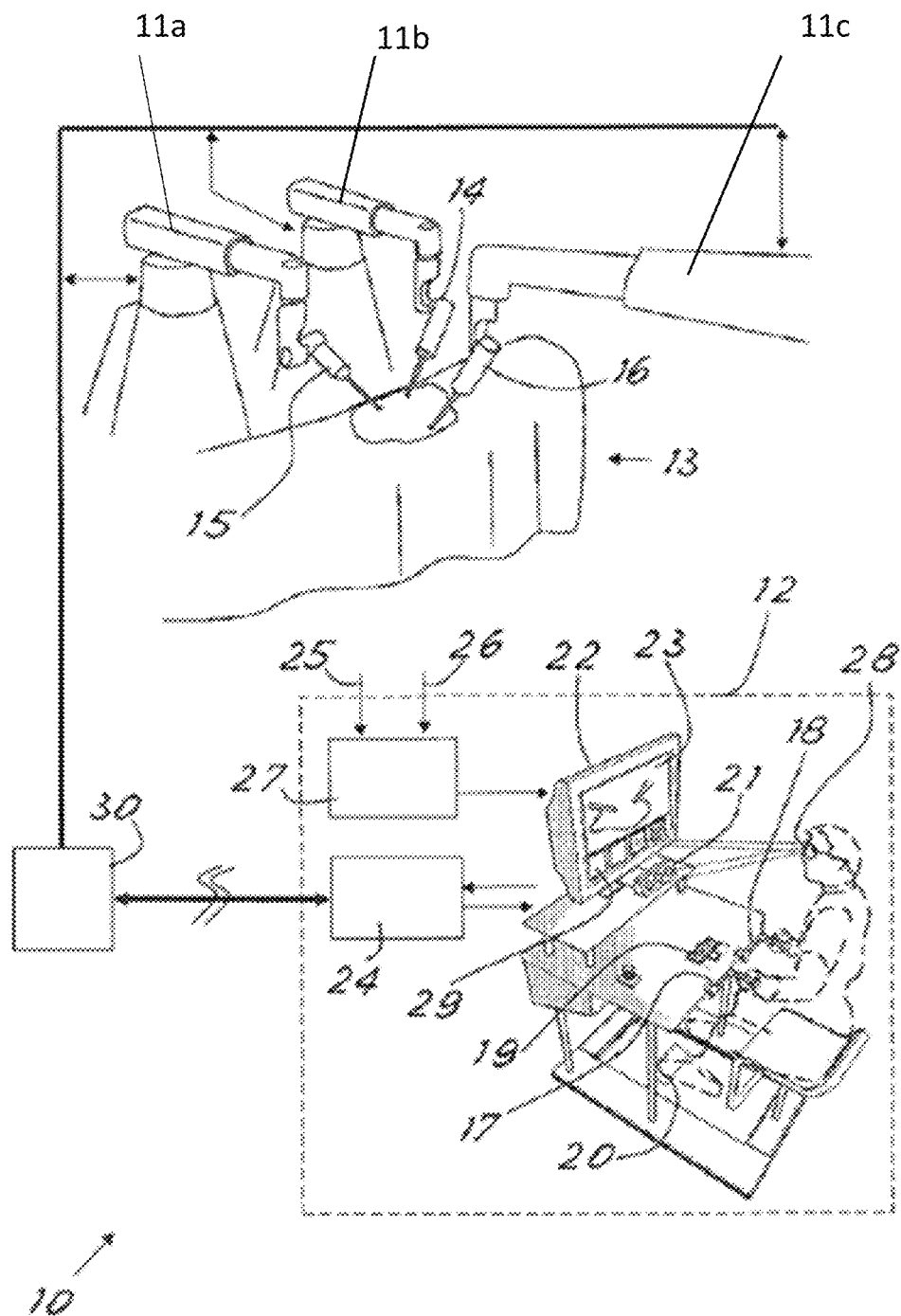
FIG. 1 is a schematic view of a robotic surgery system.

The system includes elements described in the Background section and shown in FIG. 1, namely at least one robotic manipulator or arm 11a, 11b, 11c, at least one instrument 15, 16 positionable in a work space within a body cavity by the robotic manipulator or arm, a camera 14 positioned to capture an image of the work space, and a display 23 for displaying the captured image. An input device 17, 18 or user controller is provided to allow the user to interact with the system to give input that is used to control movement of the robotic arms and, where applicable, actuation of the surgical instrument. An eye tracker 21 is positioned to detect the direction of the surgeon's gaze towards the display.

A control unit 30 provided with the system includes a processor able to execute programs or machine executable instructions stored in a computer-readable storage medium (which will be referred to herein as "memory"). Note that components referred to in the singular herein, including "memory," "processor," "control unit" etc. should be interpreted to mean "one or more" of such components. The control unit, among other things, generates movement commands for operating the robotic arms based on surgeon input received from the input devices 17, 18, 21 corresponding to the desired movement of the surgical instruments 14, 15, 16.

The memory includes computer readable instructions that are executed by the processor to perform the methods described herein. These include methods of using eye tracking input in a sequence for assigning user input devices to selected surgical instruments or robotic manipulators, and methods of using eye tracking input in a sequence for recognizing surgical instruments positioned in a surgical work site and displayed on an endoscopic display.

Assigning User Inputs to Instruments/Robotic Manipulators

Figure 3:
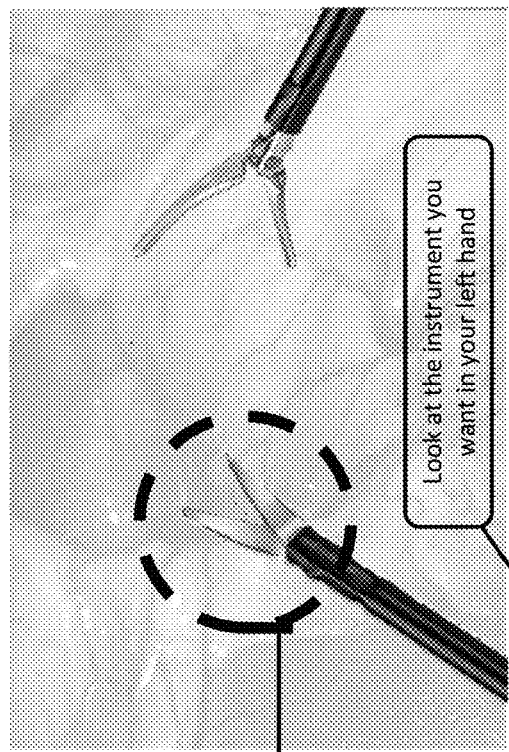
FIG. 3 is similar to FIG. 2, but additionally shows a prompting overlay.
Figure 2:
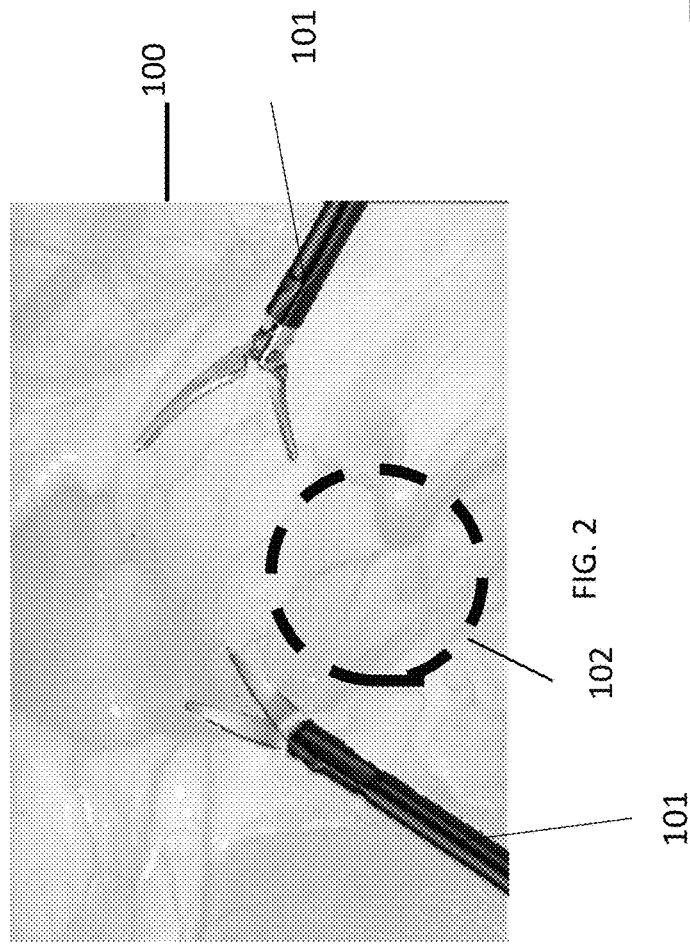
FIG. 2 depicts an image on an endoscopic display, and an overlay indicating the user's gaze location with respect to the display.
Figure 4:
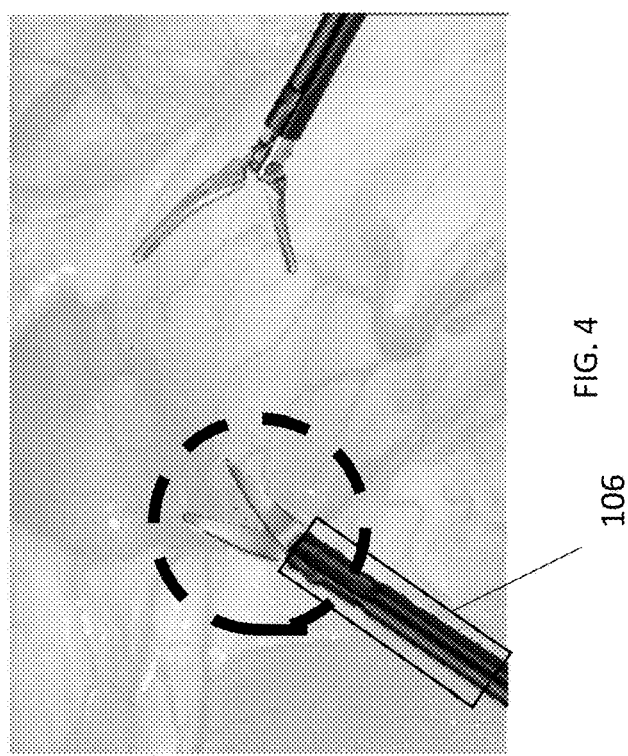
FIG. 4 is similar to FIG. 3, but the prompting overlay has disappeared, and an additional overlay is shown over the shaft of one of the instruments.

An exemplary system includes a mode of operation that allows the user to look at an instrument displayed in an endoscopic image to initiate assignment of that instrument to a given hand controller at the surgeon console. FIG. 13 is a flow diagram showing a method that can be performed by the processor during this mode of operation, in accordance with the computer readable instructions, to assign a hand controller to an instrument based on user eye gaze input. FIGS. 2-4 depict an image display displaying an endoscopic image 100 of a work area with in a body cavity during the performance of this method. The displayed image includes two instruments 101 and the surrounding tissue within the body cavity.

In general, the method starts with the system entering into an instrument pairing sequence. This can be initiated by the user or be part of an initial set-up sequence performed at the start of a procedure. As depicted in FIG. 13, the steps performed by the processor include receiving eye gaze information from the eye tracker. Step 200. This input allows the processor to determine the region of the screen the user is viewing, and thus allows it to determine, in Step 202 which of the instruments 101 on the display the user is looking at. As shown in FIGS. 2 and 3, a visual overlay 102 may be caused by the processor to be generated and displayed to provide feedback to the user about the current gaze location. The overlay is depicted as a dashed circle in the figures but may be generated in any form useful to the user. When displayed, the overlay will track the user's gaze on the endoscopic image.

In an optional step depicted in FIG. 3, the user is cued using visual or other prompts 14 to look at the instrument within the view to assign it to a given input controller. A visual prompt might be an overlay caused by the processor to be generated and displayed on the image display as shown. In the example shown in FIG. 3, the overlay cues the user with an instruction to look at the instrument to be paired with the user input device that is to be operated by the user's left hand. Other prompts might include auditory prompts, or tactile prompts such as vibration of the hand controller that is to be paired in the pairing sequence. In the sequence of steps depicted in FIG. 13, this step is performed prior to the step of determining which instrument on the display the user is looking at.

In an alternative embodiment, rather than being prompted, the user might instead input instructions to the processor directing the processor to enter a sequence of pairing a designated one of the hand controllers with an instrument. For example, if the user wishes to pair the hand controller on the user's right, the user might, after instructing the system to enter an instrument pairing sequence, first give input to the system that it is the right-hand controller that is to be paired. This may be done using an input feature on the hand controller itself, such as a button, knob or other switch. Once this input has been given to the system, the method proceeds with Step 200.

The step of determining which instrument the user is looking at may be performed using various methods. For example, when the user looks at the instrument to be assigned to a particular controller, the system may employ a computer vision algorithm to differentiate that instrument from the surrounding features in the camera image. Some computer vision algorithms that may be used for this purpose are described below, but others can be used as alternatives. In some embodiments, the instrument position(s) may be known in the endoscopic view using other means. For example, based on kinematic information the processor receives information defining, or can determine, the relative positions and orientations of the camera to the instruments within the body cavity. This allows, in Step 202, a determination of which instrument on the camera view displayed is the one the user is looking at. The system may apply a visual overlay 106 to that instrument, such as the one displayed over the image of the instrument shaft in FIG. 4, to confirm to the user that the instrument has been identified.

After it has been determined which instrument the user is looking at, that instrument is assigned to the user input device/hand controller. Step 204. If there are multiple user input devices, the user will have been prompted, as discussed in connection with FIG. 3, or will have instructed the system, as to which user input device is in the process of being assigned. Once the eye-selected instrument is paired with the relevant user input device, the processor can, upon receiving instrument input from that user input device (Step 206), transmit robot control signals that cause the robotic arm supporting the eye-selected instrument to manipulate and/or actuate that instrument.

The described sequence may be a one that is performed before system use, and it may also be performed at a later time during the surgical procedure. For example, it can be used to re-assign instruments or change pairings of instruments and user input devices mid-procedure, or to assign instruments based on repositioning of robotic arms or the patient. In some procedures the system includes a fourth manipulator arm handling a third instrument. In such procedures this assignment may also be used to swap control of an input controller from a one instrument to another instrument that is not presently assigned to an input controller.

Figure 5:
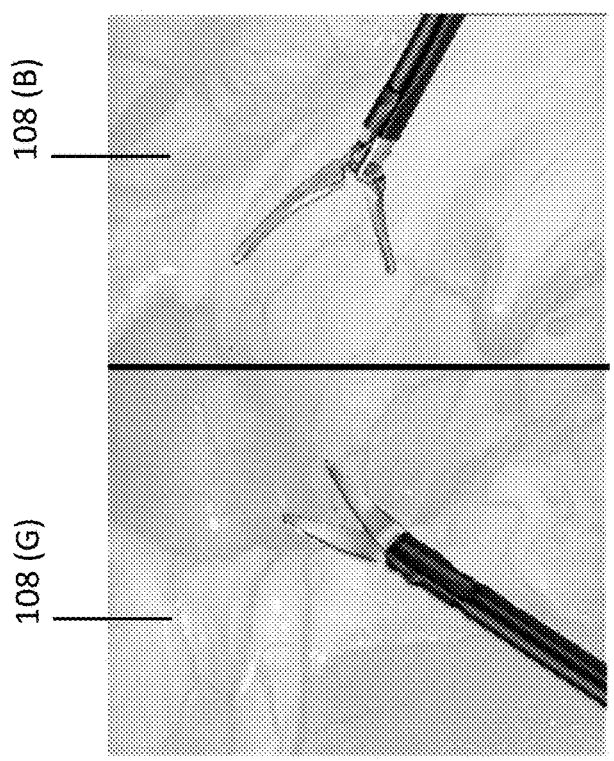
FIG. 5 depicts an image on an endoscopic display, together with a first color overlay G on the left side of the screen and a second color overlay B on the right side of the screen.

A second embodiment is one in which the instrument position(s) in the endoscopic view is/are already known or may be acquired. In accordance with this method, the system is configured such that detecting the user's gaze to a particular area of the screen (e.g. the left or right side) may be sufficient input to instruct the system to assign the instrument in that area to the appropriate hand/input controller. This method is depicted in the flow diagram of FIG. 14 and illustrated in FIG. 5. Although FIG. 5 uses the left and right halves of the screen as the defined area, smaller regions of the display may also be used. Overlays may be used to provide feedback to the user confirming the assignment, such as by briefly showing overlays above or on the assigned instrument or its region on the screen. For example, overlays 108 may cover the left and right sides of the screen, with each overlay being in a differentiating color (shown in FIG. 5 is green (G) on the left and blue (B) on the right) of the robotic manipulator arm holding the assigned instrument. In this figure, the overlaid colors inform the user that the "green arm" is holding the left-hand instrument, and the "blue arm" is holding the right-hand instrument. This overlay may be displayed temporarily or may change saturation or form/size to be less visually obstructing to the surgical scene.

FIG. 14 is a flow diagram showing this method, which can be performed by the processor according to the computer readable instructions. The method begins with the system entering into an instrument pairing sequence. This can be initiated by the user or be part of an initial set-up sequence performed at the start of a procedure. Eye gaze information is received from the eye tracker. Step 300. This input allows the processor to determine the region of the screen the user is viewing, Step 302. Because the processor has, or can obtain or determine, information as to which area of the display one or both instruments are in, it can determine, in Step 304 which of the instruments 101 on the display is in the area the user is looking at. As discussed in connection with FIG. 5, visual overlay may be caused by the processor to be generated and displayed to provide feedback to the user about the identified area of the display or the gaze location.

In an optional step, the user may be cued in a manner similar to that described with respect to FIG. 3, using visual or other prompts to look at the instrument within the view to assign it to a given input controller. A visual prompt might be an overlay caused by the processor to be generated and displayed on the image display as shown. In the example shown in FIG. 3, the overlay cues the user with an instruction to look at the instrument to be paired with the user input device that is to be operated by the user's left hand. Other prompts might include auditory prompts, or tactile prompts such as vibration of the hand controller that is to be paired in the pairing sequence. In the sequence of steps depicted in FIG. 14, this step is performed prior to the step of determining which area of the display the user is looking at.

In an alternative embodiment, rather than being prompted, the user might instead input instructions to the processor directing the processor to enter a sequence of pairing a designated one of the hand controllers with an instrument. For example, if the user wishes to pair the hand controller on the user's right, the user might, after instructing the system to enter an instrument pairing sequence, first give input to the system that it is the right-hand controller that is to be paired. This may be done using an input feature on the hand controller itself, such as a button, knob or other switch. Once this input has been given to the system, the method proceeds with Step 300.

The step of determining which instrument is in the area the user is looking at may be performed using various methods. Although computer vision algorithms described with respect to the first embodiment can be used, this embodiment is well suited to systems in which the instrument position(s) are known or can be determined in the endoscopic view using other means. For example, based on kinematic information the processor receives information defining, or from which it can determine, the relative positions and orientations of the camera to the instruments within the body cavity. This allows, in Step 304, a determination of which instrument on the camera view displayed is the one in the region the user is looking at. The system may apply a visual overlay to the region the user is looking at, or on the identified instrument (based on its known position relative to the camera), or give some other feedback to the user, to confirm to the user that the instrument has been identified.

After it has been determined which instrument the user wants to pair with the relevant hand controller, that instrument is assigned to the user input device/hand controller. Step 306. If there are multiple user input devices, the user will have been prompted, as discussed in connection with FIG. 3, or will have instructed the system, as to which user input device is in the process of being assigned. Once the eye-selected instrument is paired with the relevant user input device, the processor can, upon receiving instrument input from that user input device (Step 308), transmit robot control signals that cause the robotic arm supporting the eye-selected instrument to manipulate and/or actuate that instrument.

The described sequence may be a one that is performed before system use, and it may also be performed at a later time during the surgical procedure. For example, it can be used to re-assign instruments or change pairings of instruments and user input devices mid-procedure, or to assign instruments based on repositioning of robotic arms or the patient. In some procedures the system includes a fourth manipulator arm handling a third instrument. In such procedures this assignment may also be used to swap control of an input controller from a one instrument to another instrument that is not presently assigned to an input controller.

It should be understood that the use of eye tracking input to select an instrument may be used for other purposes besides eye tracking. For example, the eye tracking input may be used to select an instrument so that some particular action or function can be performed using that instrument, or so that that instrument can be placed in a predetermined operational mode. Actions or functions that could be performed include, without limitation, any of the following:

Clutching—the processor causes the selected instrument to be placed in a clutched state in which movement of the user input device with which that instrument is paired is temporarily suspended, allowing the user to reposition to user input device for ergonomic or other reasons;

Device Activation—the processor causes the selected instrument to deliver energy (electrical, ultrasonic, thermal, etc.) to the tissue, or to deliver staples, clips or other fasteners to the tissue, or to clamp against the tissue;

Semi-Autonomous or Autonomous modes of operation—the processor causes the selected instrument to enter into semi-autonomous modes or operation or otherwise perform autonomous or semi-autonomous actions. For example, the eye-selected instrument may be placed in a mirrored motion or matched motion mode of the type described in co-pending U.S. Ser. No. 16/236,636, filed Dec. 30, 2018 ("Dynamic Control of Surgical Instruments in a Surgical Robotic System"), or caused to apply counter-traction as described in co-pending PCT/US2018/031916 ("System and Method for Modulating Tissue Retraction Force in a Surgical Robotic System"), or to return to a predetermined home position or toggle between two predetermined positions for repetitive tasks.

Graphically tagging and recalling identified structures, as described in co-pending application Ser. No. 16/018,037 ("Method of Graphically Tagging and Recalling Identified Structures Under Visualization for Robotic Surgery").

Using Eye Tracking Input to Assist Computer Recognition of Surgical Instruments

User gaze information may be used as input to a computer vision algorithm to aid the steps of in differentiating/segmenting an instrument or other object displayed on the endoscopic display from its environment. Image segmentation is a method in which an image is separated into regions corresponding to contours or objects of interest. In the disclosed system the gaze location may identify to the computer vision algorithm the region of interest for the instrument recognition algorithm, or it may identify meaningful edges of the instrument to be recognized. The system then employs differentiation/segmentation algorithms to detect boundaries of the instrument.

Several methods may be used for image segmentation. Some methods are briefly described here merely by way of example. These will be described with respect to recognition of surgical instruments but can also be used to identify other objects within the work site.

Figure 6:
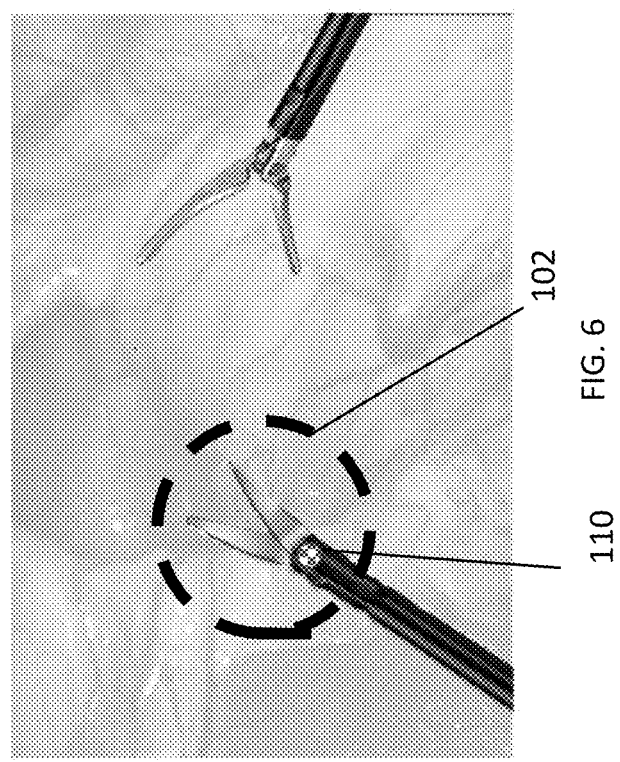
FIGS. 6-8 are a sequence of drawings depicting an image on an image display together with overlays reflecting use of a contour model to identify boundaries of an instrument.
Figure 8:
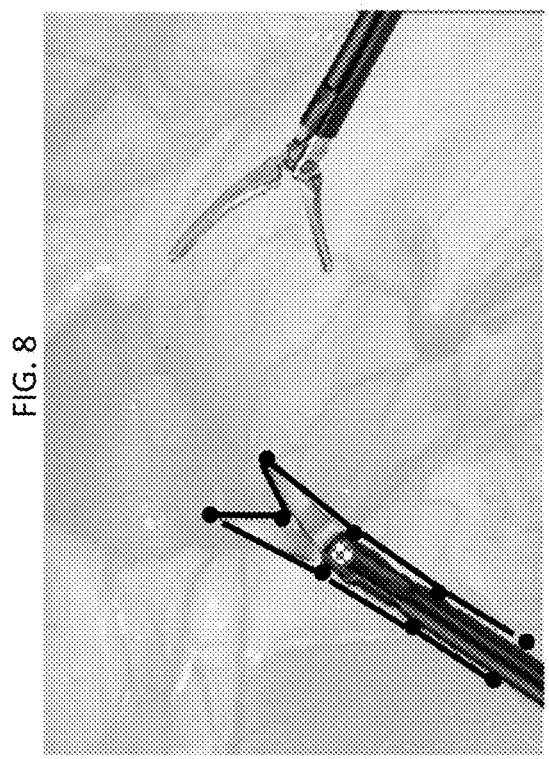
Figure 7:
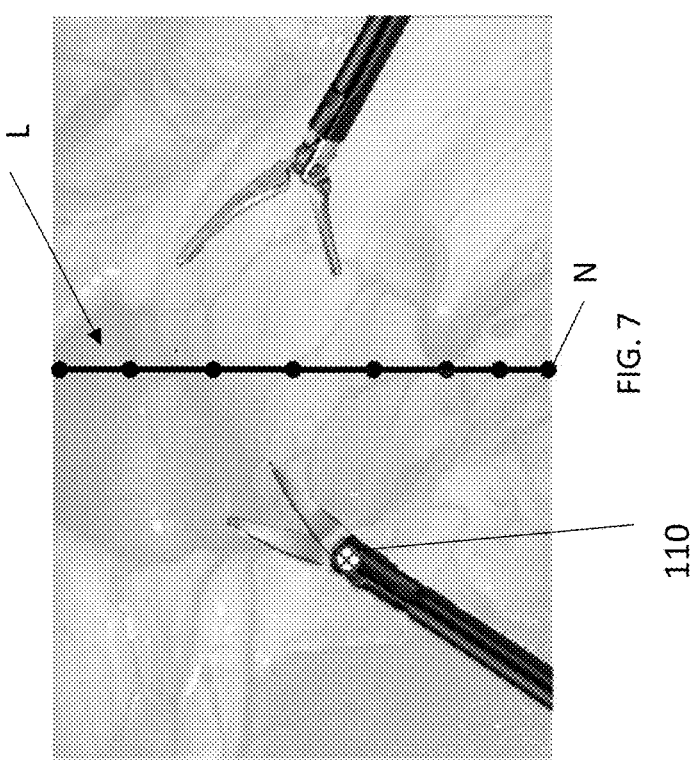
Figure 15:
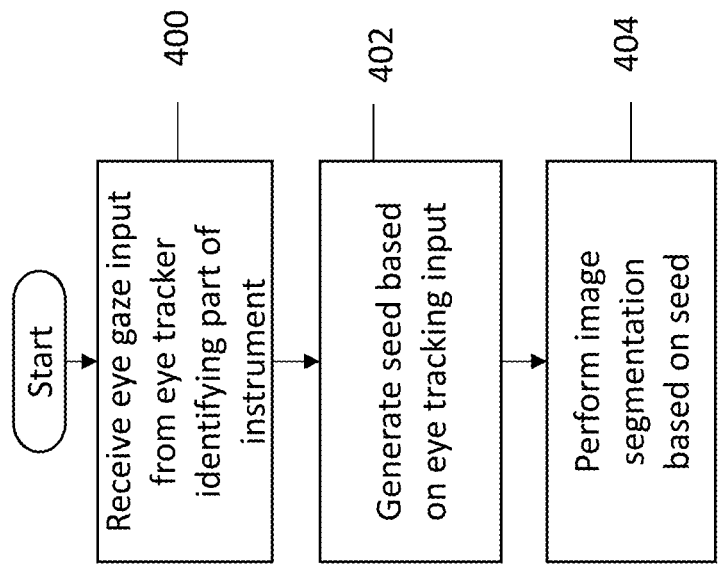
FIG. 15 is a flow diagram illustrating a method of using eye tracking input to aid in computer recognition of an object displayed on an endoscopic image display.

FIGS. 6-8 illustrate one example in which an active contour model (sometimes called a snake) is facilitated by eye gaze information. A flow diagram depicting the method performed by the processor is shown in FIG. 15. To begin, the user may be prompted to look at a region of the instrument that is to be recognized. The eye tracker detects the user's gaze towards a particular instrument on the camera display. FIG. 15, Step 400. As described in connection with the earlier embodiments, an overlay 102 may be generated to display the area on the screen that the user us looking at.

The eye gaze input from the eye tracker is used to generate a "seed." FIG. 15, Step 402. An overlay 110 may be displayed as in FIG. 7, representing the seed. This seed is recognized by the system as being within the bounds of the instrument due to the fact that the user has designated it to be as such using the eye tracking input. Image segmentation is next performed to recognize the boundaries of the instrument. FIG. 15, Step 404. FIG. 7 shows an initial state of one example of image segmentation using the active contour model. A line L with a plurality of nodes is shown. The illustrated initial placement of the contour line is made based on the basic assumption that one instrument is on the left side of the image and the other instrument is on the right side of the image. The contour moves through the image towards the seed, detecting edges of the instrument and conforming to those edges, thus creating a contoured region that contains the seed location. Parameters of "tension" between the nodes/contour shape parameter will guide the motion of the contour as it moves through the image and encounters edges. Note that the graphics shown in FIGS. 6-8 to illustrate use of the model may not be shown to the user, although the user may be shown some simplified version.

Figure 10:
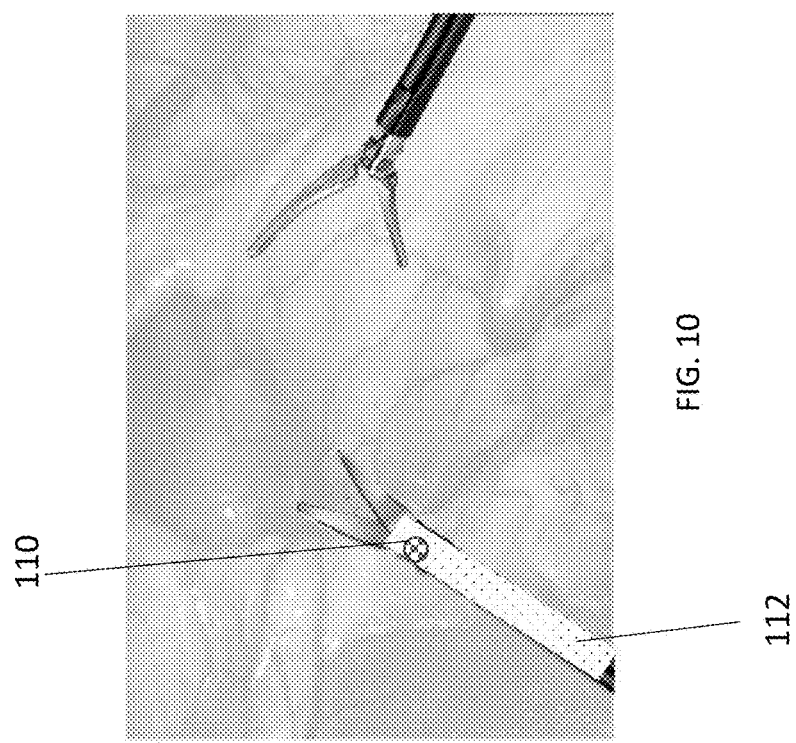
FIGS. 9-10 are a sequence of drawings depicting an image on an image display together with overlays reflecting use of a region growing algorithm to identify regions of an instrument.
Figure 9:
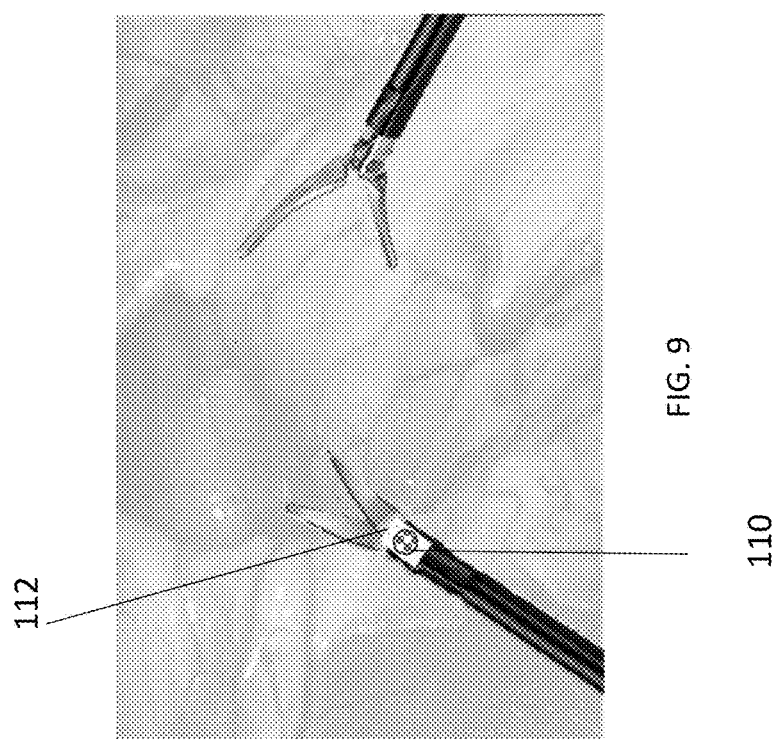

In another embodiment, the program may use gaze information to generate multiple seeds in a region-growing algorithm as an alternate, or additional, method of image segmentation. For example, as shown in FIG. 9, a seed location is identified using eye gaze as specified with respect to the prior example. It may be marked by an overlay 110 as discussed. Then the system grows the region to surrounding parts of the instrument as illustrated by the shaded region 112 around the seed in FIG. 9. Continued detection in each direction relative to the seed continues to expand the edge of the contour to the detected boundaries of the instrument in the image. FIG. 10 shows the detected region expanded closer to the boundaries of the instrument.

The shape of the region used for this model may be a simple geometric figure such as the rectangular region shown, a more complex polygon, or some other combination of lines/shapes/curves. An amorphous region that expands to the boundaries of the instrument may also be used; an example of this may be an active contour model whose initial shape lies within the instrument and expands to its boundaries. In others, more complex shapes or contours may be used. The complexity of the shape used may depend on the intended task. Thus, using a simple geometrical shape as shown may be sufficient for an instrument assignment task, but other tasks requiring more complex shape determination and differentiation (e.g. use for collision detection or surgical task assurance described in U.S. Ser. No. 16/237,444, filed Dec. 31, 2018 "System and Method for Controlling a Robotic Surgical System Using Identified Structures") may require more complex shapes or contours.

Other image segmentation means are also within the scope of this invention, and combinations of image segmentation means may also be used to improve performance.

Figure 11:
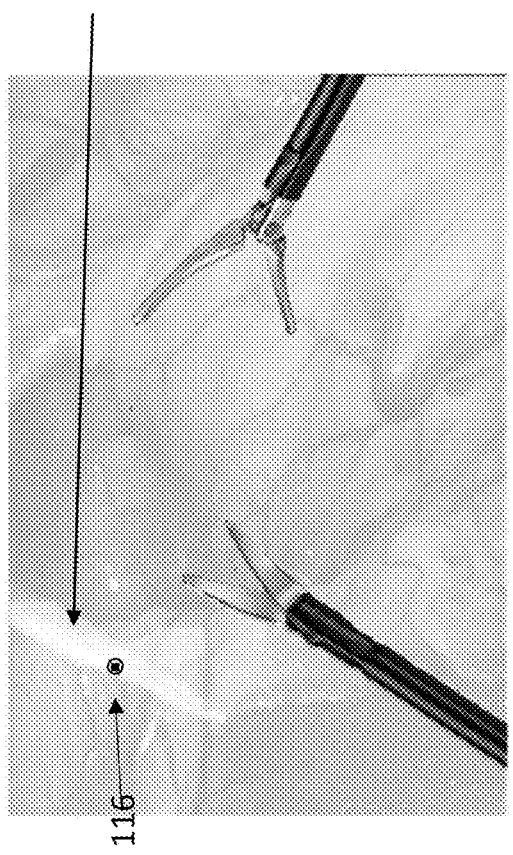
FIG. 11 depicts an image on an endoscopic display, in which a bright region marks a position of a ureter having an illumination device within in it, and in which a first overlay marks a first seed location placed using eye tracking input and used in identifying contours of the illuminated ureter.

Other uses of eye tracking may include the use of eye tracking input to differentiate between other structures in the image instead of, or in addition to, instruments. For example, in FIG. 11, a lighted ureteral stent is used to provide better visualization of the ureter. This is useful because the ureter is typically hidden below fascia and yet is a structure the surgeon wishes to avoid contacting with instruments to avoid ureteral injuries while operating deep in the pelvis. In this figure, brighter region 114 marks the lighted ureter.

Figure 12:
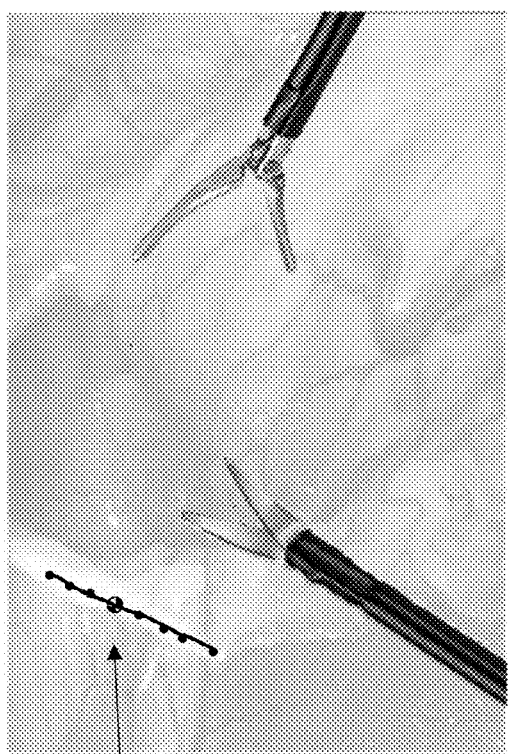
FIG. 12 is similar to FIG. 12 and shows a contour that follows the lighted ureter after image segmentation.

The user may be prompted to look at the object to be identified. The prompt may be an overlay display an instruction (e.g. "look at the lighted ureter") or some other form of prompt. The system then detects the users gaze (FIG. 15, Step 400) in order to provide seed information to a computer vision algorithm. See FIG. 11, and FIG. 15, Step 402. Active contour models, region-growing algorithms, or other means as discussed above may be used for image segmentation. FIG. 15, Step 404. FIG. 12 schematically illustrates the initial seed 116 identified using eye tracking input and a contour following the lighted ureter as a result of image segmentation. The process may be repeated for other instruments within the field. For example, new seed location may be created by tracking the user's gaze as the user looks at the image of another surgical instrument together, and contour thus being determined to follow the shape of the instrument.

In modified versions of the computer recognition embodiments, the user may give input to the system instructing the system to enter into an object-recognition or instrument-recognition mode. Following receipt of that input, the system will receive the eye gaze input to begin the process of object recognition based on the eye gaze input.

Multiple cues for a single structure, object, instrument, or region may be used to provide input to the computer vision algorithm. A plurality of prompts such as "Look along the length of the instrument", or "Look at the tip of the instrument" and "Look at the proximal end of the instrument shaft" may be used to initiate collection of eye gaze input from which multiple seed locations can be generated, or to initiate collection of eye gaze input that indicates a general direction of motion that cues the computer vision algorithm and assists with segmentation. The system may give a sequence of prompts in order to gain a plurality of eye gaze inputs to the instrument marking different parts of the instrument. An overlay may provide a visual indication of the location of the user's gaze as discussed with respect to FIG. 2.

The system may use a 2D or 3D camera. Use of a 3D camera may provide additional stereoscopic information that, when seeded with the eye tracking input, provides even more robust results from a computer vision algorithm.

The eye tracking input may be used to define planes of interest, regions of interest, structures or regions to avoid, or structures/planes to follow for use in methods of the type described in U.S. Ser. No. 16/237,444, filed Dec. 31, 2018 "System and Method for Controlling a Robotic Surgical System Using Identified Structures", and U.S. Ser. No. 16/010,388, filed Jun. 15, 2018 ("Method and Apparatus for Trocar-Based Structured Light Applications"), or it may be paired with other information, such as kinematic models, to assist a computer vision algorithm as also described in that application.

All patents and applications referred to herein, including for purposes of priority, are incorporated herein by reference.

I claim:

1. A robotic surgical system, comprising:
   at least two surgical instruments, each instrument moveable by a robotic manipulator within a work area;
   a first hand controller and a second hand controller;
   a camera positioned to capture an image of a portion of the work area;
   an image display for displaying the image;
   an eye gaze sensor positionable to detect a direction of the user's gaze towards the image of the work area on the display, and
   a processor configured to
   prompt the user to direct the user's gaze towards a portion of the displayed image at which the one of said at least two surgical instruments the user wants to assign to the first hand controller is located,
   determine, based on the direction detected by the eye gaze sensor, which of the at least two instruments displayed on the image display the user is gazing towards, and
   assign the first hand controller to the determined instrument.

2. The system of claim 1, wherein the processor is configured to receive input from the first hand controller and to control the robotic manipulator to move the instrument in response to the input.

3. The system according to claim 1, wherein the processor is configured to determine, based on the direction detected by the eye gaze sensor, which of the at least two instruments the user is viewing on the image display, and to assign the first hand controller to an instrument identified to the system using detected eye gaze.

4. The system according to claim 1, wherein the processor is configured to determine, based on the direction detected by the eye gaze sensor, the region of the image display of the work site that is occupied by the instrument the user wants to assign to the first hand controller.

5. A method of using a robotic surgical system, comprising:
   providing a first hand controller and a second hand controller;
   positioning at least two surgical instruments, within a work area, each instrument moveable by a robotic manipulator;
   capturing an image of the surgical instruments within the work area;
   displaying the image on an image display;
   prompting a user to direct the user's gaze towards a portion of the displayed image at which the one of said at least two surgical instruments the user wants to assign to the first hand controller is located;
   receiving from an eye gaze sensor input representing a direction of a user's gaze towards the image;
   determining, using the eye gaze sensor input, which of the at least two instruments displayed on the image display the user is gazing towards; and
   assigning the first hand controller to the determined instrument to enable control, using input from the first hand controller, of the robotic manipulator operatively associated with the determined instrument.

6. The method of claim 5, wherein the method further includes the step of receiving input from the first hand controller and controlling the robotic manipulator to move the determined instrument in response to the input.

7. The method according to claim 5, wherein the determining step includes determining, based on the direction detected by the eye gaze sensor, which of the at least two instruments the user is viewing on the image display, and wherein the assigning step includes assigning the first hand controller to an instrument identified to the system using detected eye gaze.

8. The method according to claim 5, wherein the determining step includes determining, based on the direction detected by the eye gaze sensor, the region of the image display of the work site that is occupied by the instrument the user wants to assign to the first hand controller.

\* \* \* \* \*